United States Patent
Yu et al.

(10) Patent No.: US 9,295,740 B2
(45) Date of Patent: Mar. 29, 2016

(54) METHOD FOR MAKING RHENIUM-186/188 LABELED HUMAN SERUM ALBUMIN MICROSPHERES AND KIT FOR MAKING THE SAME AND METHOD FOR USING THE KIT

(75) Inventors: Chia-Yu Yu, Taoyuan County (TW); Te-Wei Lee, Taoyuan County (TW); Su-Jung Chen, Taoyuan County (TW); Liang-Cheng Chen, Taoyuan County (TW); Chien-Hong Lin, Taoyuan County (TW)

(73) Assignee: INSTITUTE OF NUCLEAR ENERGY RESEARCH ATOMIC ENERGY COUNCIL, EXECUTIVE YUAN, Taoyuan County (TW)

( * ) Notice: Subject to any disclaimer, the term of this patent is extended or adjusted under 35 U.S.C. 154(b) by 696 days.

(21) Appl. No.: 13/538,105

(22) Filed: Jun. 29, 2012

(65) Prior Publication Data
US 2013/0172532 A1    Jul. 4, 2013

(30) Foreign Application Priority Data

Dec. 30, 2011    (TW) .............................. 100149875 A

(51) Int. Cl.
*A61K 51/08*    (2006.01)
*A61K 51/12*    (2006.01)

(52) U.S. Cl.
CPC ........... *A61K 51/081* (2013.01); *A61K 51/1251* (2013.01)

(58) Field of Classification Search
None
See application file for complete search history.

(56) References Cited

U.S. PATENT DOCUMENTS

2008/0219923 A1    9/2008    Wunderlich et al.

OTHER PUBLICATIONS

Rajvanshi et al., "Rapid clearance of transplanted hepatocytes from pulmonary capillaries in rats indicates a wide safety margin of liver repopulation and the potential of using surrogate albumin particles for safety analysis", Journal of Hematology 30: 299-310 (1999).*
Maus et al., "Labelling of commerically available human serum albumin kits with 68Ga as surrogates for 99mTc-MAA microspheres", Applied Radiation and Isotopes 69:171-175 (2011).*
Park et al., "Novel and efficient preparation of precursor [188Re(OH2)3(CO)3]+ for the labeling of biomolecules", Bioconjugate Chem. 17: 223-225 (2006).*
Schibli et al., Steps toward high specific activity labeling of biomolecules for therapeutic application: preparation of precursor [188Re(H2O)3(CO)3]+ and synthesis of tailor-made bifunctional ligand systems, Bioconjugate Chem. 13: 750-756 (2002).*
Gerd Wunderlich et, al., "A kit for labeling of [188Re] human serum albumin microspheres for therapeutic use in nuclear medicine", 2005, Elsevier Ltd.
Wang et, al., "Intratumoral Injection of Rhenium—188 Microspheres into an Animal Model of Hepatoma", Oct. 1998, pp. 1752-1757, vol. 39, The Journal of Nuclear Medicine.
Gerd Wunderlich et, al., "Labeling and biodistribution of different particle materials for radioembolization therapy with 188Re", 2004, Elsevier Ltd.

* cited by examiner

*Primary Examiner* — Anand Desai
(74) *Attorney, Agent, or Firm* — WPAT, PC; Justin King

(57) ABSTRACT

The present invention relates to a method for preparing $^{186/188}$Re-labeled human serum albumin (HSA) microspheres by $^{186/188}$Re(I)-tricarbonyl ion. This radioactive particle can be subjected to radioembolization for liver tumor. In this method, $^{186/188}$Re(I)-tricarbonyl ion ($^{186/188}$Re(OH$_2$)$_3$(CO)$_3$)$^+$) are employed as a precursor for directly labeling HSA microspheres with $^{186/188}$Re at appropriate temperature.

10 Claims, 8 Drawing Sheets

| kept flushing CO gas into vial (A) which contains borane ammonia ($NH_3BH_3$) | ← 401 |

| injecting $^{186/188}$Re from vial (C) into vial (A) to synthesize $[^{188}Re(CO)_3(OH_2)_3]^+$ or $[^{186}Re(CO)_3(OH_2)_3]^+$ after incubation | ← 402 |

FIG. 3A

| injecting Tween 80 into vial (B) which contains HSA microspheres. | ← 404 |

| injecting $[^{188}Re(CO)_3(OH_2)_3]^+$ or $[^{186}Re(CO)_3(OH_2)_3]^+$ into vial (B) to produce unpurified $^{186/188}$Re-HSA microspheres | ← 405 |

| purifying the $^{188}$Re-HSA microspheres or $^{186}$Re-HSA microspheres were purified by centrifuging so as to get pure $^{186/188}$Re-HSA microspheres. | ← 406 |

FIG. 3B

METHOD FOR MAKING RHENIUM-186/188 LABELED HUMAN SERUM ALBUMIN MICROSPHERES AND KIT FOR MAKING THE SAME AND METHOD FOR USING THE KIT

FIELD OF THE INVENTION

The present invention relates to relates to a method for preparing $^{186/188}$Re-labeled human serum albumin (HSA) microspheres by $^{186/188}$Re(I)-tricarbonyl ion. This radioactive particle can be subjected to radioembolization for liver tumor. In this method, $^{186/188}$Re(I)-tricarbonyl ion ($^{186/188}$Re(OH$_2$)$_3$(CO)$_3$)$^+$) are employed as a precursor for directly labeling HSA microspheres with $^{186/188}$Re at appropriate temperature.

BACKGROUND OF THE INVENTION

Radioactive microspheres radioembolization offers promise for treatment of liver cancer. Radioactively labeled microspheres are injected directly into the blood vessel feeding tumor through hepatic catheterization. The injected microspheres can emit radiation for a very limited distance and surrounding normal tissues remain unaffected. For this purpose, variety of radioisotopes including rhenium-188 ($^{188}$Re) has been used for labeling appropriate particles. $^{188}$Re is a radionuclide with a physical half-life of 16.9 h and has several advantages compared to other beta-emitting radionuclides. It emits beta particles with a maximum energy of 2.12 MeV and a 155 keV gamma ray, which are suitable for therapy and imaging. The HSA microspheres showed several advantages including biodegradable; bio-compatible; non-toxic and non-antigenic; uniform size; high mechanical stability to resist breakdown and passage through the capillary network and high chemical stability to resist radiolysis. Taken together, HSA microsphere is an ideal carrier for radionuclide.

Wang S. J. et al. described method for labeling resin microspheres with $^{188}$Re (Journal of Nuclear Medicine, 1998, 39(10): 1752-1757; Nuclear Medicine Communications, 1998, 19: 427-433). In this protocol, large amount of tin salt was used to radioactively labeling; however it may cause unexpected pharmacological effects. In addition, the acidify condition would hydrolyze proteins. Wunderlich et al. (Applied Radiation and Isotopes 2005, 62: 745-750; Applied Radiation and Isotopes 2005, 62: 915-918, Nuclear Medicine and Biology 2010, 37: 861-867; U.S. Patent: US20080219923 A1) disclosed $^{188}$Re labeled HSA microspheres. In this protocol, the radio-labeling process was carried out by combination of the reductive reaction of Re(VII) with Sn(II) and a particle surface-related co-precipitation effect of tin hydroxid colloid with reduced, hydrolyzed rhenium. The labeling yield is significantly higher and the amount of tin sale used in reaction is limited. However, in vitro stability is not stable. The particle-bound radioactivity was decreased to 86% within 48 hrs at ambient temperature. Hence, $^{188}$Re or tin chloride may release from microsphere surface and cause side effects.

SUMMARY OF THE INVENTION

To enhance in vivo stability of $^{188}$Re labeled HSA microspheres, this invention introduce $^{186/188}$Re(I)-tricarbonyl ion ($^{186/188}$Re(OH$_2$)$_3$(CO)$_3$)$^+$) as a precursor for HSA microspheres radio-labeling. Principally, the weakly bound H$_2$O ligands of [$^{186/188}$Re(OH$_2$)$_3$(CO)$_3$]$^+$ can be rapidly replaced by histidine or cycteine groups with N, O and S electron donors on HSA microspheres. According to this invention, $^{186/188}$Re was covalently bound to the surface of HSA microspheres. The particle-bound radioactivity of $^{186/188}$Re-HSA microspheres were remained above 95% after 72 hours incubation at 37° C. The radioactivity of $^{186/188}$Re-HSA microspheres in the liver was maintained above 85% ID after 72 hour post-injection. The method described in this invention can efficiently enhance the stability of radioactive HSA microspheres in vitro and in vivo. Furthermore, this invention provided a convenient method for radio-labeling of HSA microspheres with $^{186/188}$Re as well as a kit for manufacturing.

By means of the method, $^{186/188}$Re(I)-tricarbonyl ion ($^{186/188}$Re(OH$_2$)$_3$(CO)$_3$)$^+$) is employed as a precursor for directly labeling HSA microspheres with $^{186/188}$Re to form $^{186/188}$Re-HSA microspheres. In this invention, the amino borane-reduced $^{188}$ReO$_4^-$ was interacted with carbon oxide to form [$^{186/188}$Re(OH$_2$)$_3$(CO)$_3$]$^+$. $^{186/188}$Re-HSA microspheres can be prepared by reacting [$^{186/188}$Re(OH$_2$)$_3$(CO)$_3$]$^+$ with HSA microspheres at appropriate temperature.

In this invention, the kit for preparing $^{186/188}$Re labeled microspheres comprises the following 3 bottles: Vial (A) containing amino borane (NH$_3$BH$_3$) is designed for $^{186/188}$Re (I)-tricarbonyl ion synthesis; Vial (B) containing HSA microspheres is designed for labeling HSA microspheres with $^{186/188}$Re(I)-tricarbonyl ion; Vail (C) containing $^{186/188}$Re solution. The advantages of this invention include convenient for manufacturing; in vitro and in vivo stability; capable of radiotherapy and diagnosis; available for multi-dose treatment.

This invention provided a method for preparing $^{186/188}$Re-HSA microspheres. According to this method, $^{186/188}$Re(I)-tricarbonyl ion ($^{186/188}$Re(OH$_2$)$_3$(CO)$_3$)$^+$) are employed as a precursor for directly labeling HSA microspheres with $^{186/188}$Re at appropriate temperature.

According to this invention, the kit of performing the method for labeling HSA microspheres with $^{186/188}$Re includes 3 bottles: Vial (A) containing amino borane (NH$_3$BH$_3$) is designed for $^{186/188}$Re(I)-tricarbonyl ion synthesis; Vial (B) containing HSA microspheres is designed for labeling HSA microspheress with $^{186/188}$Re(I)-tricarbonyl ion; Vail (C) containing $^{186/188}$Re solution.

In one example of this invention, the kit of labeling HSA microspheres with $^{186/188}$Re was performed as following procedures: Vail (A) was kept flushing with CO gas. $^{186/188}$Re solution withdrawed from Vail (C) was added into Vail (A). The solution mixture in Vial (A) was incubated at appropriate temperature. Vial (B) containing HSA microspheres was suspended with Tween-80. $^{186/188}$Re(I)-tricarbonyl ion synthesized from Vial (A) was injected into Vial (B). $^{186/188}$Re-HSA microspheres were produced and purified at appropriate temperature.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention and wherein:

FIG. 3A indicated the flowchart of preparation for $^{186/188}$Re(I)-tricarbonyl ion.

FIG. 3B indicated the flowchart of preparation for $^{188}$Re-HSA microspheres.

DESCRIPTION OF THE EXEMPLARY EMBODIMENTS

For your esteemed members of reviewing committee to further understand and recognize the fulfilled functions and structural characteristics of the invention, several exemplary embodiments cooperating with detailed description are presented as the follows.

Example 1

Preparation of HSA Microspheres

The pure refine olive oil (800 ml) was placed in a 1000 ml flat-bottomed glass beaker and warmed up to 100° C. with stirring (420 rpm) for one hour. Then olive oil was cooled to 60° C. and HSA (80 mg) was dissolved in 5 ml distilled water. HSA solution was added dropwise to the oil by tubing pump at a flow rate of 4-9 ml/min with constant stirring (550 rpm). The solution was reacted at 60° C. with 420 rpm stirring speed for 30 min. The processes of cross-linking were as following: the solution was heated up to 70° C. and constant stirred at 100 rpm for 1 hour; then heated up to 80° C. and stirred at 80 rpm for 1 hour; finally heated up to 110° C. and stirred at 50 rpm for 0.5 hour. To remove all traces of oil, the HSA microspheres were vacuum filtered onto 20 μm filter and washed with 200 ml acetone, then air-dried with oven at 40° C. for 15 min. The dried HSA microspheres were sieved to three different size range (53 μm, 32 μm and 20 μm). Finally the yield of 20-to-53 μm fraction of HSA microspheres was 17%.

Example 2

Figure 1:
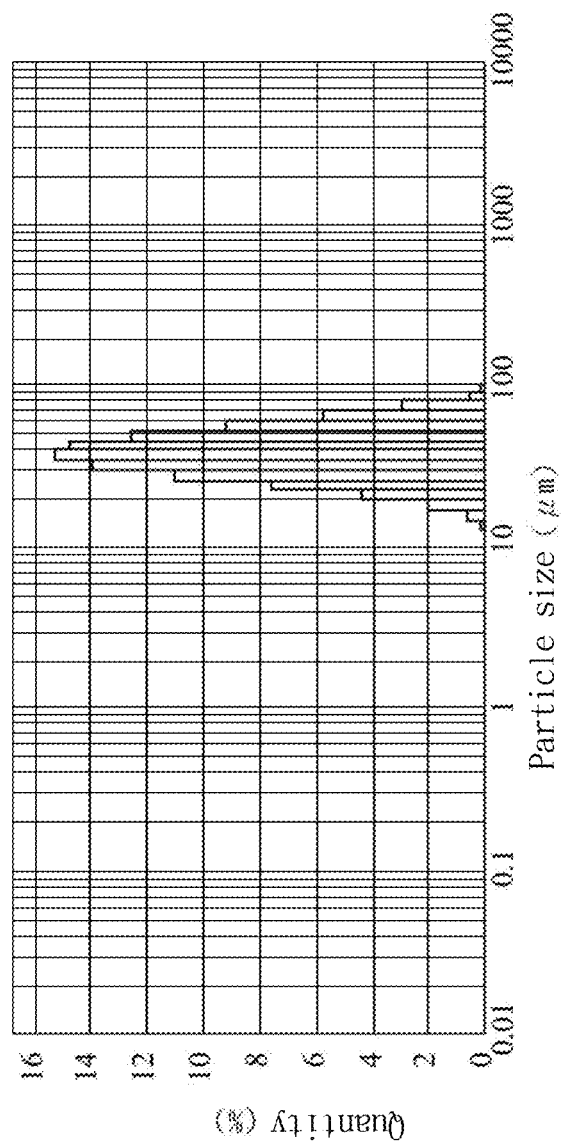
FIG. 1 shows the distribution of HSA microspheres in view of particle size that are prepared using a method of the present invention.

Determination of Particle Size and Conformation of HSA Microspheres (1) Particle size analysis-Malvern mastersizer:
By means of Fraunhofer Diffraction method, the diffraction scatting angle of the particle is on proportion to the particle-size when a bunch of micron particles pass through a beam of light. The size of particles can be measured by detecting various intensities of diffracted beam superimposition of various diffraction angles with the photo-sensor. (Malvern) mastersizer 2000 was used to analyze HSA microspheres. HSA microspheres (10 mg/ml) were injected to measuring cell. The HSA microspheres suspension were formed particle flow by continuous cycle of flow and pass the light beam and measure the particle size. According to the method for preparing HSA microspheres, particles were distributed between 24 and 60 μm particle size. The maximum average particle size distribution was 40 μm, as shown in FIG. 1.

Figure 2B:
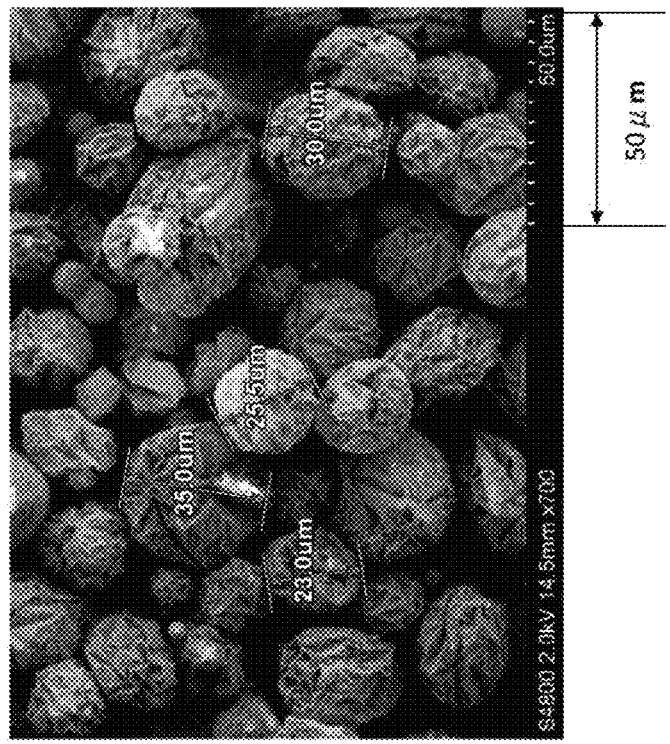
FIG. 2A and FIG. 2B are SEM images of HSA microspheres that are magnified by 3000 times and 700 time in respective.
Figure 2A:
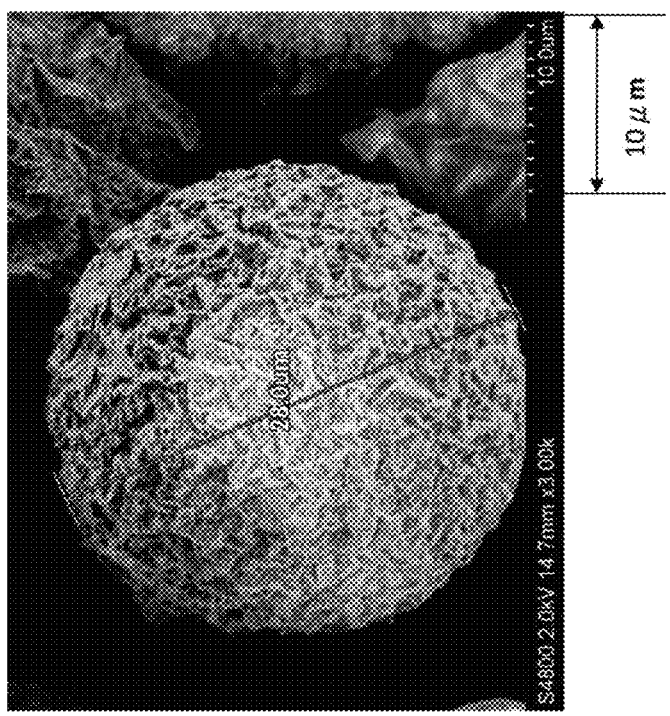

(2) Conformation analysis-Scanning Electron Microscope (SEM):
HSA microspheres were analyzed with Scanning Electron Microscope (HITACH S-4800 SEM). Proper amount of specimen is mounted on a specimen stub using electrically conductive double-sided adhesive tape. Specimen stub was putted into the chamber of SEM. Specimen was excited by secondary electron under vacuum environment. And then, the surface image of specimen can be projected on the screen. The voltage and current for measurement is 10 volt and 2 A. The working distance width is 15 mm. According to the method for preparing HSA microspheres, the shape of particle was rough surfaced sphere or oval-shaped. The particle size was distributed between 20~35 μm. The result corresponded to the particle size measured by mastersizer. The SEM images of FIGS. 2A and 2B were at a magnification of 3000× and 700×, respectively.

Example 3

Preparation of $[^{186/188}Re(CO)_3(OH_2)_3]^+$

Figure 3:
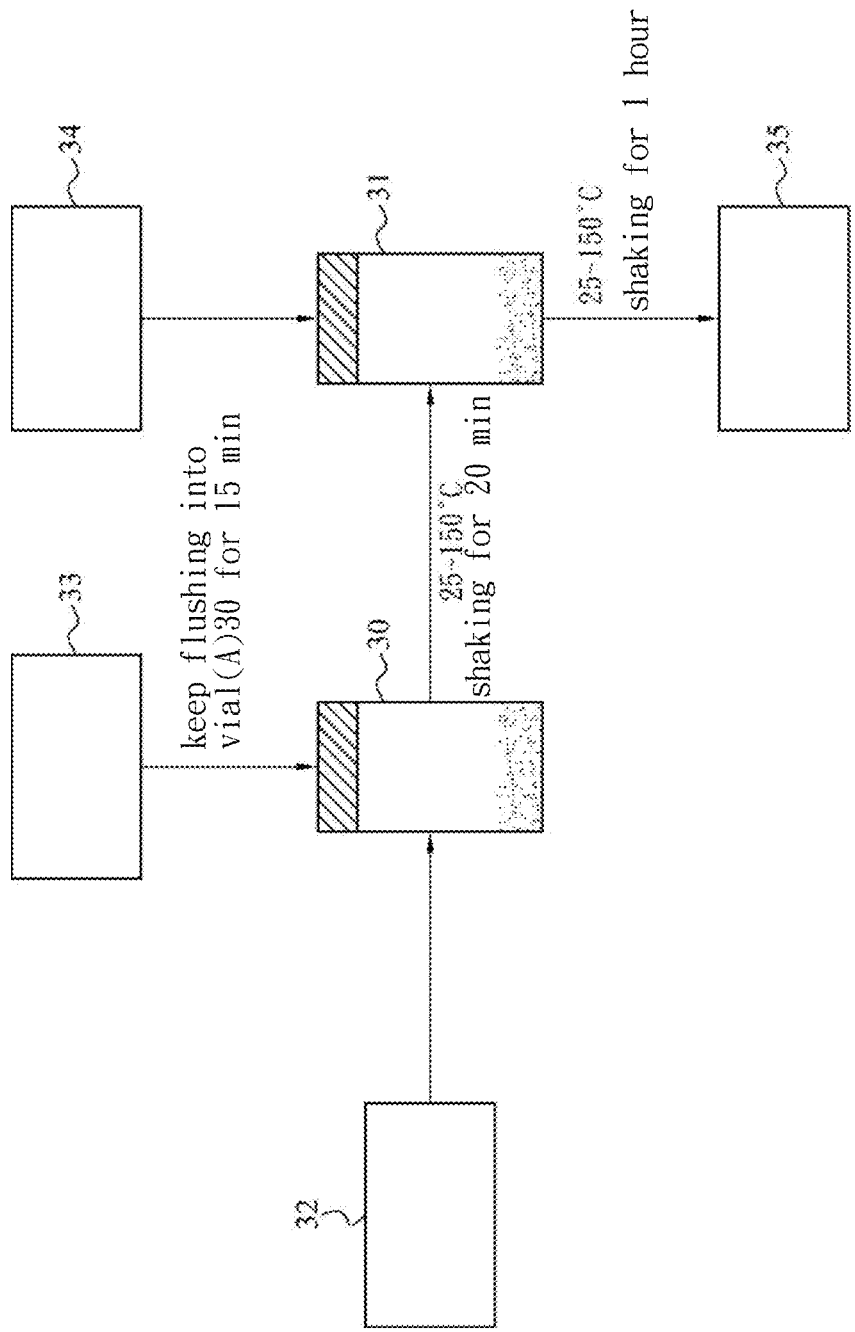
FIG. 3 indicated the scheme of preparation for $^{188}$Re-HSA microspheres.

The processes for preparing $[^{186/188}Re(CO)_3(OH_2)_3]^+$ were shown as FIG. 3 and FIG. 3A. FIG. 3 indicated the scheme of preparation for $^{186/188}$Re-HSA microspheres; FIG. 3A indicated the flowchart of preparation for $^{186/188}$Re(I)-tricarbonyl ion, which included the step 401 as following: CO gas kept flushing into vial (A) containing borane ammonia (NH$_3$BH$_3$). In this example, borane ammonia (8 mg; NH$_3$BH$_3$) was placed in a 5-ml vial (A). The vial (A) was sealed with an aluminum-capped rubber stopper and flushed with 1 atm CO gas for 15 min; the pressure of CO gas in vial (A) was sustained through a balloon flushed with CO gas inserted in the rubber stopper. According to step 402, $^{186/188}$Re from vial (C) was injected into vial (A) to synthesize $[^{186/188}Re(CO)_3(OH_2)_3]^+$ after incubation. In this example, $^{188}$ReO$_4^-$ in vial (C) was eluted from a $^{188}$W/$^{188}$Re with saline. About 1 ml of sterilely filtered $^{188}$Re perrhenate (1~20 mCi) dissolved in 0.9% NaCl and 7 μl 85% Phosphoric acid were injected through the rubber stopper into vial (A). The solution mixture in vial (A) was incubated in a shaking water bath at 25-150° C. for 20 min with 80 rpm. After cooling down to room temperature, the solution mixture was analyzed with high-performance liquid chromatography (HPLC).

Figure 4A:
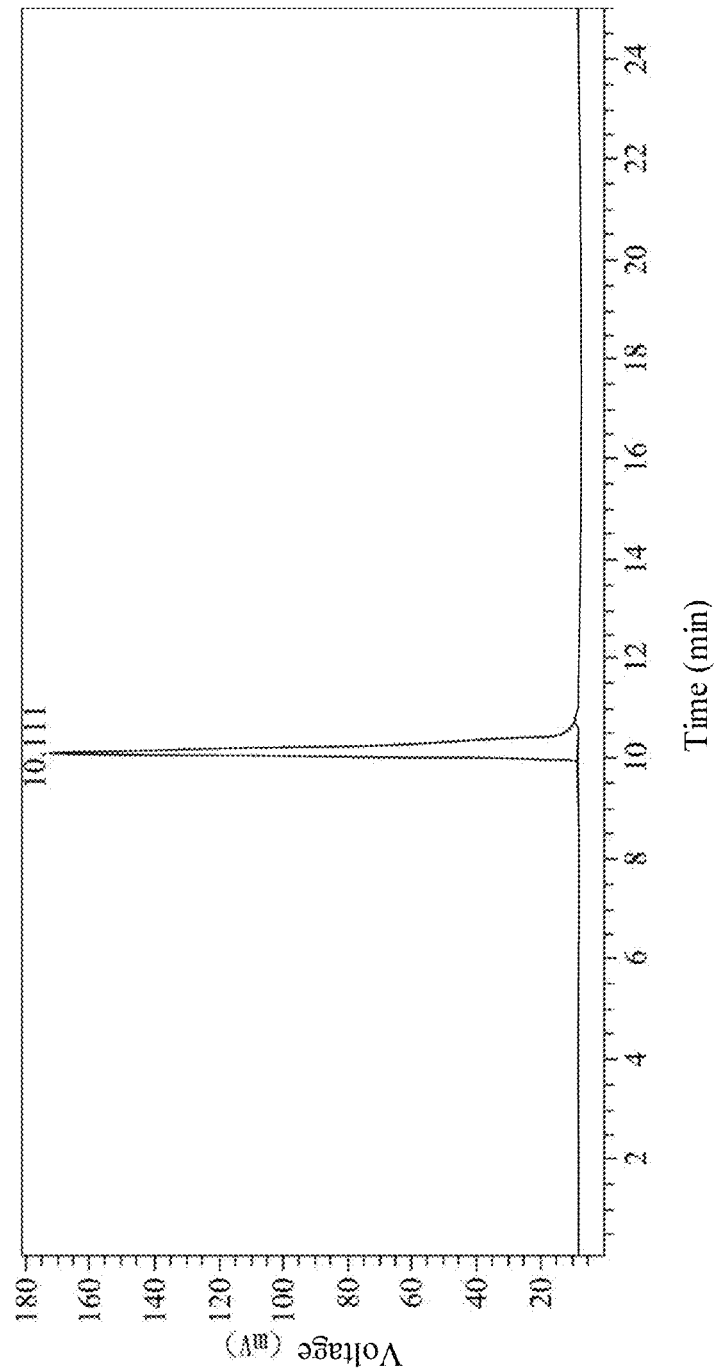
FIG. 4A indicated the RP-HPLC-UV chromatography of free $^{188}$Re.
Figure 4B:
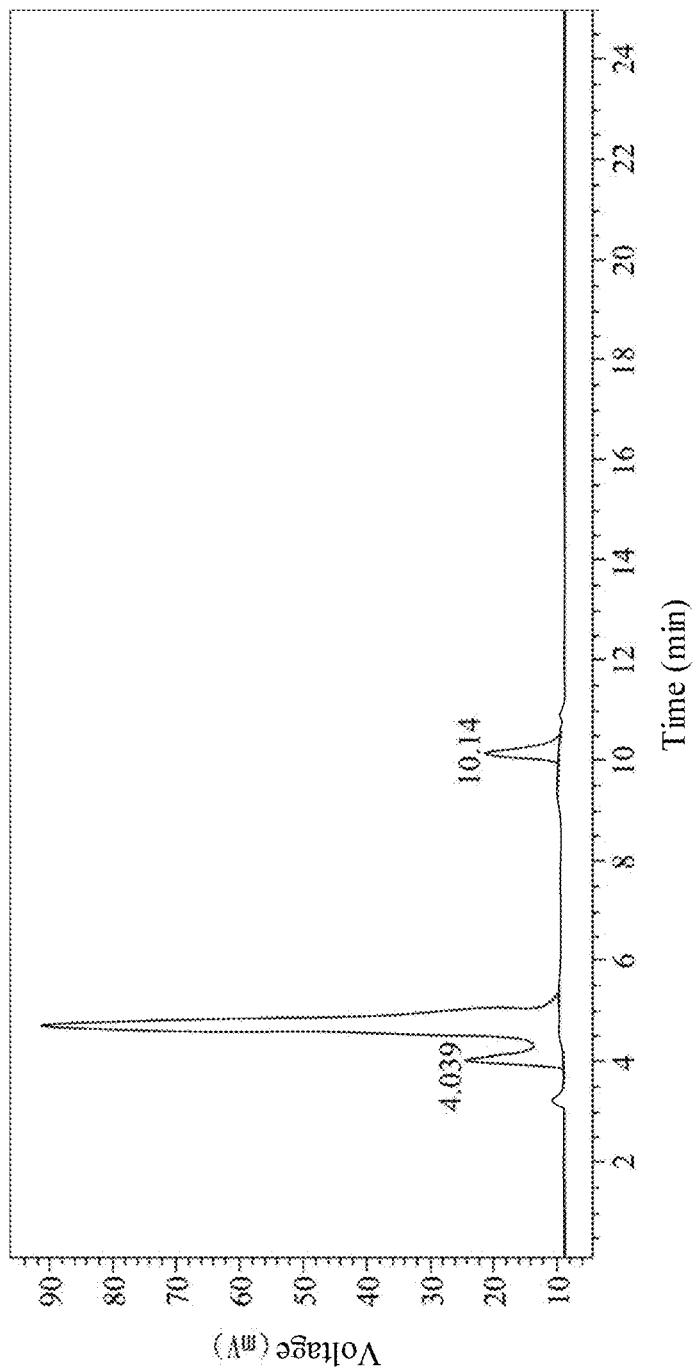
FIG. 4B indicated the RP-HPLC-UV chromatography of $[^{188}Re(CO)_3(OH_2)_3]^+$.

In this example, the yield of $[^{188}Re(CO)_3(OH_2)_3]^+$ was analyzed by high-performance liquid chromatography (HPLC) using a RP C-18 column (Vydac 218TP, 10μ, 250× 4.6 mm) by a Waters HPLC system equipped with a radiometric detector. The eluent consisted of methanol and 0.05 M triethylammonium phosphate (TEAP) buffer pH 2.25. The gradient elution started with 100% of 0.05 M TEAP buffer from 0 to 5 min and switched at 6 min to 75% of 0.05 M TEAP buffer and 25% of methanol. At 9 min it switched to 66% of 0.05 M TEAP buffer and 34% of methanol, followed by a linear gradient program from 66% of 0.05 M TEAP buffer to 0% of 0.05 M TEAP buffer and 100% of methanol at 15 min. Then sustain 100% of methanol for 5 min. The flow rate was 1 ml/min. The retention time of $^{188}$Re perrhenate ($^{188}$ReO$_4^-$) was 10.1~10.19 min, the retention time of [$^{188}$Re(CO)$_3$(OH$_2$)$_3$]$^+$ was 4.65~4.71 min as shown in FIGS. 4A and 4B. FIG. 4A indicated the RP-HPLC-UV chromatography of free $^{188}$Re; FIG. 4B indicated the RP-HPLC-UV chromatography of [$^{188}$Re(CO)$_3$(OH$_2$)$_3$]$^+$. The yield of [$^{188}$Re(CO)$_3$(OH$_2$)$_3$]$^+$ was 75~80%. The method for preparing [$^{186}$Re(CO)$_3$(OH$_2$)$_3$]$^+$ was the same as the method for [$^{188}$Re(CO)$_3$(OH$_2$)$_3$]$^+$.

Example 4

Preparation of $^{186/188}$Re-HSA Microspheres

The processes for preparing $^{186/188}$Re-HSA microspheres were shown as FIG. 3 and FIG. 3B. FIG. 3 indicated the kit of preparation for $^{186/188}$Re-HSA microspheres; FIG. 3B indicated the flowchart of preparation for $^{186/188}$Re-HSA microspheres which included steps as following: according to the step 404, Tween 80 was injected into vial (B) containing HSA microspheres. HSA microspheres (10 mg) were placed in a glass vial (B) and suspended with 2.4 mg Tween 80 dissolved in 0.5 ml 0.9% NaCl. Then according to step 405, [$^{186/188}$Re(CO)$_3$(OH$_2$)$_3$]$^+$ was injected into vial (B) to produce unpurified $^{186/188}$Re-HSA microspheres. In this example, vial (B) was sealed with an aluminum-capped rubber stopper and flushed N$_2$ gas for 2~4 min. About 450 µl [$^{188}$Re(CO)$_3$(OH$_2$)$_3$]$^+$ from vial (A) was injected into vial (B). The solution mixture in the vial was incubated in water bath at 25~150° C. for 1 hour with shaking (150 rpm). After incubation, according to the step 406, the $^{188}$Re-HSA microspheres were purified by centrifuging to get pure $^{188}$Re-HSA microspheres. After the analysis of radio-labeling efficiency, the supernatant was removed by centrifuging (9400×g, 5 min) and pellet was washed with 0.9% NaCl for twice. Finally, the $^{188}$Re-HSA microspheres were suspended with 0.9% NaCl and subjected to determine the radioactivity and concentration.

The radio-labeling efficiency was determined as follow: Add 500 µl unpurified $^{188}$Re-HSA microspheres suspension into a Protein LoBind tube (Eppendorff), the suspension was centrifuged for 5 min at 10,000 min$^{-1}$ and aspirated 100 µl supernatant into another tube. The activity of 100 µl supernatant and remaining sample (400 µl supernatant and radiolabeled particles) was determined separately by activimeter (CRC-15R form Capintec, Inc. Ramsey, N.J., USA). The labeling efficiency of $^{188}$Re-HSA microspheres were calculated as following: [activity of the remainder−(activity of the 100 µl supernatant×4)]/total activity×100%. The labeling efficiency of $^{188}$Re-HSA microspheres in this method was more than 85%. The method for preparing $^{186}$Re-HSA microspheres was the same as the method for $^{188}$Re-HSA microspheres.

Example 5

Figure 5:
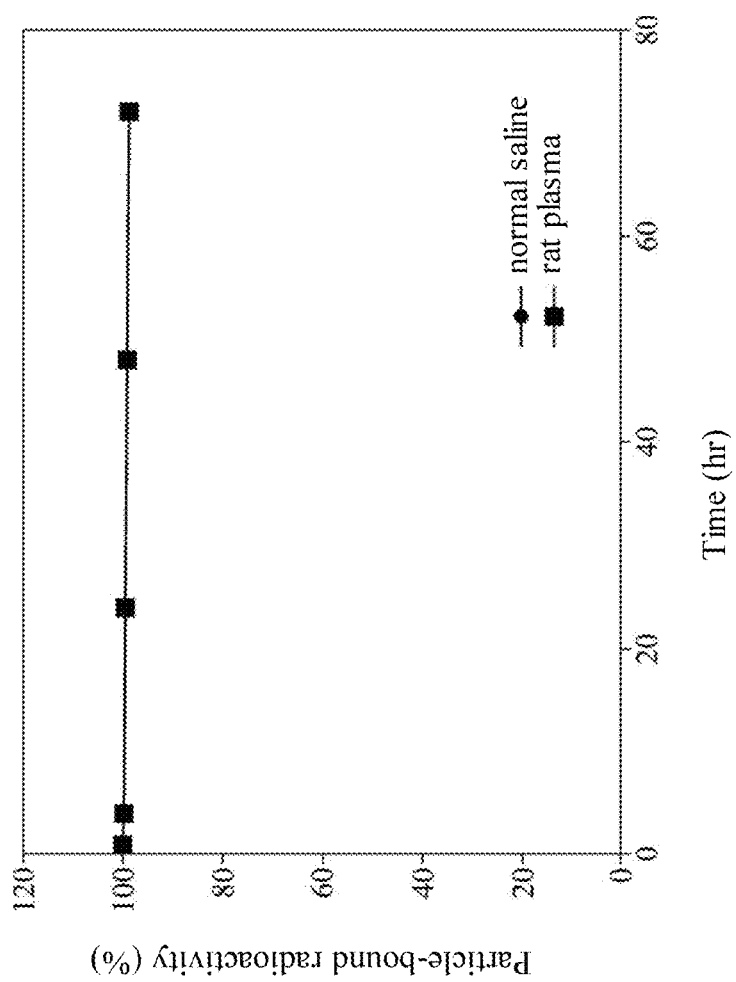
FIG. 5 shows a result of stability analysis for $^{188}$Re labeled HSA microspheres.
Figure 6:
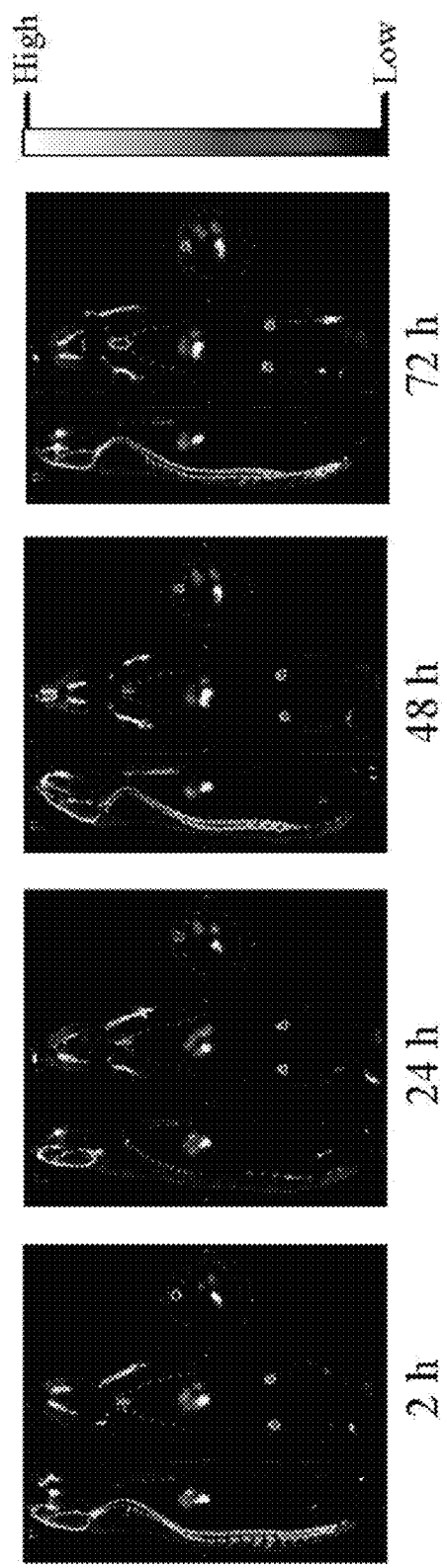
FIG. 6 representative NanoSPECT/CT images of rat with N1-S1 hepatoma at 2-72 h by injected with $^{188}$Re-HSA microspheres (589 μCi/200 μL) via hepatic artery route.

In Vitro Stability of $^{188}$Re-HSA Microspheres (i) In rat plasma: Mixing 150 µl $^{188}$Re-HSA microspheres suspension and 2.85 ml rat plasma, and transfer 490 µl mixture into new Protein LoBind tube (Eppendorff). The tubes were incubated at 37° C. in a Thermomixer (Ependorff) with shaking (600 rpm). (ii) In normal saline: Adding 490 µl $^{188}$Re-HSA microspheres suspension into new Protein LoBind tube and mixed well. Particle bound activity was analyzed at 1, 4, 24, 48 and 72 hour. Particle bound activity was determined as follows: An aliquot of 150 µl $^{188}$Re-HSA microspheres was placed in a Protein LoBind tube, the suspension was centrifuged for 5 min at 10,000 min$^{-1}$. Then an aliquot of 50 µl was carefully withdrawn from the supernatant. The activity of 50 µl supernatant and remaining sample (100 µl supernatant and radiolabeled particles) were determined separately by activimeter (CRC-15R form Capintec, Inc. Ramsey, N.J., USA). The particle bound activity was calculated as follows: [activity of the remainder−(activity of the 50 µl supernatant× 2)]/total activity×100%. After 72 hours of incubation at 37° C. or at room temperature, the $^{188}$Re labeled HSA microspheres were found to be stable in vitro in normal saline and rat plasma because 98-99% of $^{188}$Re is still particle-bounded for up to 72 hours of incubation. In vitro stability of $^{188}$Re labeled HSA microspheres was shown at FIG. 5. The horizontal axis was represented as time interval and the longitudinal axis was represented as the average of particle-bound radioactivity (%)±standard deviation (%).

| Time (h) | Particle-bound radioactivity, mean ± SD (%) | |
|---|---|---|
| | In normal saline, 25° C. | In rat plasma, 37° C. |
| 1 | 99.88 ± 0.01 | 99.88 ± 0.09 |
| 4 | 99.76 ± 0.01 | 99.69 ± 0.05 |
| 24 | 99.29 ± 0.08 | 99.52 ± 0.06 |
| 48 | 99.00 ± 0.03 | 99.16 ± 0.19 |
| 72 | 98.91 ± 0.10 | 98.64 ± 0.11 | avaerage value ± standard deviation (SD), n = 3

In vitro stability of $^{188}$Re labeled HSA microsphere in (●) normal saline at room temperature and in (■) rat plasma at 37° C. Particle bound activity was analyzed at 1, 4, 24, 48 and 72 hour.

Example 6

Nano-SPECT/CT Imaging and Quantification Analysis of $^{188}$Re-HSA Microspheres The rat was anesthetized with 1-2% isoflurane in 100% O$_2$ and injected with $^{188}$Re-HAS microspheres via hepatic artery route. Imaging was acquired at 1, 24, 48 and 72 hr after injection of $^{188}$Re-HSA microspheres. When the imaging acquisition, the rat were anesthetized with 1-2% isoflurane in 100% O$_2$. The rat was positioned prone in the scanner. Nano-SPECT imaging was acquired using nine multipinholes gamma-detectors and high-resolution collimators. The energy window was set at 155 KeV±10%, the image size was set at 256×256, and the field of view (FOV) of 62 mm×270 mm. For SPECT images quantification analysis, known radio-activity $^{188}$Re was performed as reference by Nano-SPECT/CT imaging. The results of images quantification analysis were presented as percentage of injection dose (% ID). The % ID was determined from the regions of interest (ROI) on the liver area with uptake (MBq). The % ID was calculated according to the following standard formula:

[Measured Activity of Live Area(MBq)/Injected Dose (MBq)]*100%

In Nano-SPECT/CT images, the obvious uptakes in liver area were observed from 2 to 72 h after injection with $^{188}$Re-HSA microspheres. The result of images quantification analysis were indicated that the % ID was maintained at 95% ID-88% ID from 2 to 72 h after injection with $^{188}$Re HSA microspheres. In this invention, $^{186/188}$Re(I)-tricarbonyl ion ($^{186/188}$Re(OH$_2$)$_3$(CO)$_3$)$^+$) is employed as a precursor for directly labeling HSA microspheres with $^{186/188}$Re to produce $^{186/188}$Re-HSA microspheres. The weakly bound H$_2$O ligands of [$^{186/188}$Re(OH$_2$)$_3$(CO)$_3$]$^+$ can be rapidly replaced by histidine or cycteine groups with N, O and S electron donors on HSA microspheres. According to this invention, $^{186/188}$Re can be covalently bound to the surface of HSA microspheres. The particle-bound radioactivity of $^{186/188}$Re-HSA microspheres was maintained above 95% after 72 hours incubation at 37° C. The method described in this invention can successfully enhance the stability of radioactive HSA microspheres in vitro and in vivo. Furthermore, this invention provided a convenient method for radio-labeling of HSA microspheres with $^{186/188}$Re as well as a kit for manufacturing.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

What is claimed is:

1. A method for preparing 186/188Re labeled HSA microspheres, the method comprising:
    reacting 186/188Re(I)-tricarbonyl ions with Human Serum Albumin (HSA) microspheres to produce 186/188Re-HSA microspheres.

2. The method according to claim 1, wherein the HSA microspheres are dried particles with a diameter of 0.1 µm to 10000 µm.

3. The method according to claim 1, wherein said reaction step is performed at a temperature of 25-150° C.

4. The method according to claim 1, further comprising using said 186/188Re-HSA microspheres as a radiotherapeutic and diagnostic agent for cancer.

5. The method according to claim 2, the method further comprising the steps of:
    keep flushing vial (A) with CO gas;
    adding 186/188Re solution withdrawn from vial (C) into vial (A);
    incubating the mixture solution in vial (A) at an appropriate temperature;
    suspending HSA microspheres in vial (B) with polysorbate 80; and
    injecting 186/188Re(I)-tricarbonyl ion synthesized from vial (A) into vial (B) to produce and purify 186/188Re-HSA microspheres at appropriate temperature.

6. The performing method according to claim 5, wherein the appropriate temperature is 25-150° C.

7. The performing method according to claim 5, wherein 186/188Re-HSA microspheres can be radiotherapeutic and diagnostic agent for cancer disease.

8. The method of claim 1, further comprising:
    providing a first vial with borane ammonia (NH3BH3);
    providing a second vial with dried HSA microspheres;
    flushing said first vial with CO gas;
    adding a solution of 186/188Re in saline to said first vial to create an 186/188Re(I)-tricarbonyl ion solution;
    adding polysorbate 80 to said second vial to create a suspension of said HSA microspheres;
    injecting said 186/188Re(I)-tricarbonyl ion solution from said first vial into said second vial create 186/188Re-HSA microspheres; and
    purifying said 186/188Re-HSA microspheres.

9. The method according to claim 8, wherein said injecting step is performed at a temperature of 25-150° C.

10. The method according to claim 8, further comprising using said 186/188Re-HSA microspheres as a radiotherapeutic and diagnostic agent for cancer.

* * * * *